United States Patent
Tarasev et al.

(10) Patent No.: US 11,662,353 B2
(45) Date of Patent: May 30, 2023

(54) METHOD FOR ASSESSING THE EFFECTS OF HYPOXIA ON TISSUES

(71) Applicant: Functional Fluidics Inc., Detroit, MI (US)

(72) Inventors: Michael Tarasev, Pinckney, MI (US); Lucas Gelmini, Sterling Heights, MI (US)

(73) Assignee: Functional Fluidics Inc., Detroit, MI (US)

( * ) Notice: Subject to any disclaimer, the term of this patent is extended or adjusted under 35 U.S.C. 154(b) by 282 days.

(21) Appl. No.: 17/016,849

(22) Filed: Sep. 10, 2020

(65) Prior Publication Data
US 2022/0074955 A1 Mar. 10, 2022

(51) Int. Cl.
*G01N 33/72* (2006.01)
*C12Q 1/26* (2006.01)
(Continued)

(52) U.S. Cl.
CPC ............. *G01N 33/721* (2013.01); *C12Q 1/26* (2013.01); *G01N 33/4925* (2013.01);
(Continued)

(58) Field of Classification Search
CPC .. G01N 33/721; G01N 33/80; G01N 33/5005; G01N 33/4925; G01N 2021/755;
(Continued)

(56) References Cited

U.S. PATENT DOCUMENTS 5,744,056 A 4/1998 Venkateshwaran et al.
5,876,604 A 3/1999 Nemser et al.
(Continued)

FOREIGN PATENT DOCUMENTS

WO 2005/100263 A1 10/2005
WO 2011/046963 A1 4/2011
(Continued)

OTHER PUBLICATIONS

Buis, "The Atmosphere: Getting a Handle on Carbon Dioxide", Oct. 9, 2019, NASA. (Year: 2019).*
(Continued)

*Primary Examiner* — Gary B Nickol
*Assistant Examiner* — Amelia Nicole Dickens
(74) *Attorney, Agent, or Firm* — Reising Ethington P.C.

(57) ABSTRACT

A method for assessing an effect of hypoxia on a tissue includes providing a sample of the tissue in a hermetically sealed container, determining a first amount of a reaction substrate (e.g., protocatechuic acid) to be introduced into the sealed container and determining a second amount of a reaction enzyme (e.g., protocatechuate dioxygenase) to be introduced into the sealed container. The method further includes introducing the reaction substrate and the reaction enzyme into the sealed container. At least one of the first amount of the reaction substrate and the second amount of the reaction enzyme is selected to induce at least one of a predetermined amount of hypoxia less than anoxia and a predetermined rate of hypoxia in the tissue during a reaction between the reaction substrate and the reaction enzyme. Values of properties of the tissue can be measured before and after the reaction to assess effects of hypoxia.

27 Claims, 7 Drawing Sheets

(51) Int. Cl.
    *G01N 33/50* (2006.01)
    *G01N 33/80* (2006.01)
    *G01N 21/75* (2006.01)
    *G01N 33/49* (2006.01)

(52) U.S. Cl.
    CPC ......... *G01N 33/5005* (2013.01); *G01N 33/80* (2013.01); *G01N 2021/755* (2013.01); *G01N 2203/0025* (2013.01); *G01N 2203/0067* (2013.01); *G01N 2333/90241* (2013.01)

(58) Field of Classification Search
    CPC ... G01N 2203/0025; G01N 2203/0067; C12Q 1/26
    See application file for complete search history.

(56) References Cited

U.S. PATENT DOCUMENTS

| | | | |
|---|---|---|---|
| 6,162,396 | A | 12/2000 | Bitensky et al. |
| 6,638,434 | B2 | 10/2003 | Otsuki et al. |
| 2011/0269159 | A1* | 11/2011 | Campbell ............... G01N 33/74 435/7.1 |

FOREIGN PATENT DOCUMENTS

| | | |
|---|---|---|
| WO | 2014/134503 A1 | 9/2014 |
| WO | 2015/054378 A1 | 4/2015 |

OTHER PUBLICATIONS

Andreou et al. "Lipoxygenases—Structure and reaction mechanism", Sep. 18, 2009, Phytochemistry, vol. 70, p. 1504-1510. (Year: 2009).*

Millett et al. "Heme-containing dioxygenases involved in tryptophan oxidation", Feb. 20, 2012, Current Opinion in Chemical Biology, vol. 16, p. 60-66. (Year: 2012).*

Torres-Guzman et al. "Peculiarities of nitronate monooxygenases and perspectives for in vivo and in vitro applications", Oct. 16, 2021, Applied Microbiology and Biotechnology, vol. 105, p. 8019-8032. (Year: 2021).*

Askoxylakis et al. "Investigation of tumor hypoxia using a two-enzyme system for in vitro generation of oxygen deficiency", 2011, Radiation Oncology, vol. 6 No. 35, p. 1-12. (Year: 2011).*

Francis et al. "The Biochemistry of the Metabolic Poison Propionate 3-Nitronate and Its Conjugate Acid, 3-Nitropropionate", Jul. 29, 2013, IUBMB Life, p. 759-768. (Year: 2013).*

Tarasev, Michael et al., "Individual Variability in Response to a Single Sickling Event for Normal, Sickle Cell, and Sickle Trait Erythrocytes," 191 Translational Research pp. 96-107 (Mar. 1, 2017). Made of record in IDS filed Apr. 12, 2021. (Year: 2017).*

Aitken, Colin Echeverria et al., "An Oxygen Scavenging System for Improvement of Dye Stability in Single-Molecule Fluorescence Experiments," 94 Biophysical Journal No. 5 pp. 1826-1835 (Mar. 2008). Made of record in IDS filed Apr. 12, 2021. (Year: 2008).*

Patil, Pravin V., et al. "The Use of Protocatechuate Dioxygenase for Maintaining Anaerobic Conditions in Biochemical Experiments," 286 Analytical Biochemistry No. 2 pp. 187-192 (Nov. 15, 2000). Made of record in IDS filed Apr. 12, 2021. (Year: 2000).*

Swoboda Marko, et al., "Enzymatic Oxygen Scavenging for Photostability Without pH Drop in Single-Molecule Experiments," 6 ACSNANO No. 7 pp. 6364-6369 (Jun. 18, 2012). Made of record in IDS filed Apr. 12, 2021. (Year: 2012).*

Askoxylakis et al. "Investigation of tumor hypoxia using a two-enzyme system for in vitro generation of oxygen deficiency", 2011, Radiation Oncology, vol. 6 No. 35, p. 1-12. Made of record in PTO-892 mailed Oct. 18, 2022. (Year: 2011).*

Aitken, Colin Echeverria et al., "An Oxygen Scavenging System for Improvement of Dye Stability in Single-Molecule Fluorescence Experiments," 94 Biophysical Journal No. 5 pp. 1826-1835 (Mar. 2008).

Brody, Aaron L., "The Use of Oxygen Scavengers and Active Packaging to Reduce Oxygen Within Internal Package Environments," (Sep. 1995).

Bull, Christopher et al., Purification and Properties of Protocatechuate 3,4-Dioxygenase from Pseudomonas Putida, 256 Journal of Biological Chemistry No. 24 pp. 12673-12680 (1981).

Choudhury, Ryan, "Hypoxia and Hyperbaric Oxygen Therapy: A Review," 11 International Journal of General Medicine pp. 431-442 (Nov. 20, 2018).

Cruz, Renato Souza et al., "Oxygen Scavengers: An Approach on Food Preservation," from Structure and Function of Food Engineering (Ayman Amer Eissa ed.), Intech, pp. 21-42 (2012).

Dalziel, K. et al., "Side Reactions in the Deoxygenation of Dilute Oxyhaemoglobin Solutions by Sodium Dithionite," 67 Biochem J. No. 1 pp. 119-124 (1957).

Dalziel K. et al., "The Kinetics of Deoxygenation of Human Haemoglobin," 78 Biochem. J. No. 2 pp. 236-245 (Feb. 1961).

Etzion, Zipora et al., "Effects of Deoxygenation on Active and Passive Ca2+ Transport and on the Cytoplasmic Ca2+ Levels of Sickle Cell Anemia Red Cells," 92 J. Clin. Invest. No. 5 pp. 2489-2498 (Nov. 1993).

Hofrichter, James, et al., "Kinetics and Mechanism of Deoxyhemoglobin S Gelation: A New Approach to Understanding Sickle Cell Disease," 71 Proc. Natl. Acad. Sci. USA No. 12 pp. 4864-4868 (Dec. 1974).

Huang, Zhi et al., "Kinetics of Increased Deformability of Deoxygenated Sickle Cells Upon Oxygenation," 85 Biophysical Journal pp. No. 4 pp. 2374-2383 (Oct. 2003).

Karimi, Afzal et al., "Enzymatic Scavenging of Oxygen Dissolved in Water: Application of Response Surface Methodology in Optimization of Conditions," 18 Chemical Industry & Chemical Engineering Quarterly No. 3 pp. 431-439 (2012).

Kaul, Dhananjaya K., et al., "Rate of Deoxygenation and Rehologic Behavior of Blood in Sickle Cell Anemia," 77 Blood No. 5 pp. 1353-1361 (Mar. 15, 1991).

McGoron, Anthony J. et al. Dehydration of Mature and Immature Sickle Red Blood Cells During Fast Oxygenation/Deoxygenation Cycles; Role of KCl Cotransport and Extracellular Calcium, 95 Blood No. 6, pp. 2164-2168 (Mar. 15, 2000).

Morris, Christopher L. et al., "Deoxygenationl-Induced Changes in Sickle Cell-Sickle Cell Adhesion," 81 Blood No. 11 pp. 3138-3145 (Jun. 1, 1993).

Papageorgiou, Dimitrios P. et al., "Simultaneous Polymerization and Adhesion Under Hypoxia in Sickle Cell Disease," 115 Proceedings of the National Academy of Sciences No. 38 pp. 9473-9478 (Sep. 18, 2018).

Patil, Pravin V., et al. "The Use of Protocatechuate Dioxygenase for Maintaining Anaerobic Conditions in Biochemical Experiments," 286 Analytical Biochemistry No. 2 pp. 187-192 (Nov. 15, 2000).

Rotman, H.H. et al., "Kinetics of Oxygenation and Deoxygenation of Erythrocytes Containing Hemoglobin S," 21 Respiration Physiology No. 1 pp. 9-17 (Jul. 1974).

Salhany, J. Mitchell et al., "The Deoxygenation Kinetics of Hemoglobin Partially Saturated With Carbon Monoxide," 247 Journal of Biological Chemistry No. 21 pp. 6985-6990 (Nov. 10, 1972).

Salhany, J. M. et al., "The Rate of Deoxygenation of Red Blood Cells: The Effect of Intracellular 2,3-Diphosphoglycerate and PH," 16 FEBS Letters No. 4 pp. 257-261 (Sep. 1, 1971).

Swoboda Marko, et al., "Enzymatic Oxygen Scavenging for Photostability Without pH Drop in Single-Molecule Experiments," 6 ACSNANO No. 7 pp. 6364-6369 (Jun. 18, 2012).

Tarasev, Michael et al., "Individual Variability in Response to a Single Sickling Event for Normal, Sickle Cell, and Sickle Trait Erythrocytes," 191 Translational Research pp. 96-107 (Mar. 1, 2017).

Tarasev, Michael et al., "The 'Bridging' Aspartate 178 in Phthalate Dioxygenase Facilitates Interactions Between the Rieske Center and the Fe(II)-Mononuclear Center," 45 Biochemistry No. 34 pp. 10208-10216 (Aug. 29, 2006).

Vandergriff, Kim D. et al. "Hemogloblin-Oxygen Equilibrium Curves Measured During Enzymatic Oxygen Consumption," 256 Analytical Biochemistry No. 1 pp. 107-116 (1998).

(56) References Cited

OTHER PUBLICATIONS

Watanabe, Hama et al., "Hemoglobin Phase of Oxygenation and Deoxygenation in Early Brain Development Measured Using fNIRS," 114 Proceedings of the National Academy of Sciences pp. E1737-E1744 (Feb. 14, 2017).

* cited by examiner

METHOD FOR ASSESSING THE EFFECTS OF HYPOXIA ON TISSUES

BACKGROUND OF THE INVENTION a. Field of the Invention

This disclosure relates to methods for assessing the effects of hypoxia on tissue. In particular, this disclosure relates to a method employing a reaction substrate such as protocatechuic acid (PCA) and a reaction enzyme such as protocatechuate dioxygenase (PCD) to create hypoxia in tissue to allow for assessment of hypoxia in the tissue.

b. Background Art

Hypoxia in medicine is a condition where tissues or organs experience depleted oxygen supply. It can be either systemic, in that it would affect the whole organism, or localized, in that it would affect only a particular tissue, organ or body part. Conditions under normal atmospheric oxygen pressure are typically referred to as "normoxia", and conditions with extremely low or no oxygen are referred to as "severe hypoxia", or "anoxia". As used herein, "hypoxia" refers to any condition with less than a normoxic amount of oxygen present while an "amount of hypoxia" or "level of hypoxia" refers to a decreased oxygen concentration (or oxygen partial pressure below normoxic), with "increased" hypoxia referring to lower oxygen tension and "severe hypoxia" referring to conditions with less that 5% of normoxic partial oxygen pressure.

Hypoxia is an integral part of the normal cell physiology. In blood, hypoxic conditions arise during oxygen delivery, reflected in oxygen saturation changes between arterial and venous blood. Tissue hypoxia can be elevated when compensatory mechanisms are not able to support the demand for oxygen—for example during strenuous exercise. Tissue hypoxia can also be affected by external conditions such as low atmospheric oxygen at high altitude. Tissue hypoxia may also change as a result of pathology, due to a desirable or undesirable effect of a drug, or as a result of cell membrane damage and/or modification. Cell membrane damage can be caused, for example, by blood storage, ex-vivo manipulation blood, or in-vivo interaction with implanted medical devices.

Physiological levels of hypoxia differ between different tissues and organs. While oxygen pressure ($PtO_2$) of 108-104 mm Hg had been reported for alveoulus, pressures of 90±5 mm Hg and 40±5 mm Hg have been reported for arterial and venous blood correspondingly. Furthermore, oxygen pressures of 61.2 mm Hg for small and 56.7 mm Hg for large bowels, 40-55 mm Hg for liver, 30-48 mm Hg for brain, ~29 mm Hg for muscles, and 22 mm Hg in the eye, etc have been reported for specific organs. As can be seen, the variability in $PtO_2$ is very significant, and often needs to be accounted for even when dealing even with healthy individuals. It should be noted, that $PtO_2$ levels may change due to environmental conditions or the type of activity, with e.g. cortical $PtO_2$ ranging from 20-25 mm Hg at rest up to 48 mm Hg during intense physical activity. As mentioned, differences in $PtO_2$ are not always the result of normal physiology, but also can be a result of a pathology (e.g. cancer, respiratory disorders, hemoglobinopatias).

One of the tissues that is affected by hypoxia is blood, particularly erythrocytes (Red Blood Cells (RBC)), with hypoxia in that case effecting changes in oxygen load of the blood oxygen carrier, hemoglobin (Hb). Clinically, the potential of harmful effects of blood hypoxia (hypoxemia) are well recognized, as well as the possibility of harm from elevated oxygen content due to excess oxygen administration.

When occurring in blood, hypoxic conditions bring about a re-equilibration between plasma oxygen and the level of hemoglobin (Hb) oxygenation. Lower external oxygen tension (partial oxygen pressure, $PtO_2$) leads to lower concentration of the oxygenated form of Hb (Oxy-Hb) and to increased concentration of the deoxygenated form of Hb (Deoxy-Hb). It is sometimes desirable to investigate the effects of hypoxia on erythrocytes and/or on hemoglobin, whether contained within erythrocytes or free in a solution such as in blood plasma or in an additive storage solution as used for packed RBC storage for blood transfusion.

Hypoxia in blood (hypoxemia) results in deoxygenation of hemoglobin with hemoglobin oxygenation/deoxygenation level being tightly correlated with partial oxygen concentration/pressure ($PtO_2$). Hemoglobin deoxygenation (percent of deoxygenated Hb form or conversably percent of oxygenated Hb form), can be estimated using well-known oxygen-hemoglobin dissociation curves. Note, that while the dependence on oxygen is in fact sigmoidal, it can be assumed to be linear between ~15 and 35-40 mm Hg for simplicity of estimations in that range. The dependence is influenced by physiological factors like pH or 2,3-Diphosphoglycerate (2,3-DPG), that cause a shift of dissociation curve, that cumulatively regulate oxygen uptake and delivery. Thereafter, it would be understood that the level of hypoxia can be associated with a corresponding concentration of deoxygenated or conversely oxygenated hemoglobin, and vice versa, with further understanding, that higher precision of calculations can be achieved by accounting for other factors affecting oxygen-hemoglobin dissociation cure. Level of hypoxia can be directly measured using, for example, oxygen sensors, and level of oxygenation/deoxygenation can be directly measured using spectrophotometry.

As mentioned above, tissue hypoxia may change as a result of pathology. For example, Sickle Cell Disease (SCD), a hereditary blood disease, can impact blood hypoxia, especially in organs such as the spleen. SCD is caused by a mutation in the HBB gene responsible for the production of hemoglobin (Hb), resulting in the so-called "sickled" RBC, which contain an abnormal Hb form, called sickle hemoglobin (HbS). Polymerization of deoxygenated Hb in cells with sufficiently high content of 14, HbS disrupts normal oxygenation-deoxygenation cycle (e.g., by altering the kinetics of deoxygenated Hb interaction with membrane structural elements) and causes RBC deformations, typically resulting in development of a sickle-like cell shape, which gave the disease its name.

Over time, sickling of or RBC results in a vastly reduced erythrocyte lifespan, down to about 20 day from the normal average of 110-120 days. Additionally, a vast array of SCD-related complications, including life-threatening, are the result of this reduced erythrocyte lifespan. For example, the potential of such hypoxia-induced polymerization to cause plasma membrane damage had been proposed previously. Cycles of HbS deoxygenation with associated polymerization and re-oxydation with polymer melting were shown to critically impact membrane structural proteins, like Band-3 complex, resulting in membrane microvecicu-lation.

Hypoxia is an integral part of SCD pathophysiology, leading to a wide range of SCD-associated complication including vaso-occlusive phenomenon. Tissue oxygenation, and thus resultant oxygen tension in patients with SCD may differ from that on non-SCD subjects due to compromised total oxygen carrying capacity of SCD blood compounded by possible changes in microcirculation e.g. due to vessel total or partial blockage due to elevated cell adhesion to endothelium. That may led to a wider deviations from "steady-state" tissue oxygenation levels at times of elevated oxygen consumption in tissues or organs, when physiological compensatory mechanisms can not fully compensate for decrease oxygen availability, exasperated by e.g. reduced RBC numbers/lower total Hb concentration and the presence of irreversibly deformed RBC. The percentage of sickled cells after deoxygenation is the basis of the standard "sickling assay" (where sickling can be induced by either low oxygen tension of change in pH) and had been used previously as a predictor of disease outcomes. Notably, the amount of sickling would significantly depend on the level of hypoxia, with more severe hypoxia resulting in more sickling, and thus potentially in more membrane damage.

The influence of hypoxia in SCD is not limited to just that arising from HbS polymerization. The interaction of deoxygenated form (Deoxy) of HbS with cytoplasmic domain of band 3 protein (cdb3) is much stronger than that of adult hemoglobin HbA, with a portion of Deoxy HbS being irreversibly bound to the complex. Even the reversibly bound fraction of Deoxy HbS has been shown to dissociate much more slowly than did Deoxy HbA, impacting sickle RBC membrane properties. Production of superoxide, facilitated under hypoxic conditions and exacerbated in SCD, is a source of potential oxidative damage to the membrane. Oxidative damage causes a multitude of defects in membrane structures critically involved in regulation of erythrocyte membrane stability and function. Previously, Reactive Oxygen Species (ROS)-induced damage was linked with irreversible micro-rheologic abnormalities of sickle RBC membranes. Abnormal HbS-membrane interactions have also been associated with the decline of nitric oxide (NO) and antioxidant bioavailability, and has been suggested as a key factor in accelerated sickle RBC senescence. It had been suggested, that cycles of hypoxia, with consequent chronic and systemic oxidative stress, repeatedly generating great amounts of ROS, could lead to a cyclic cascade, characterized by elevated cell adhesion, hemolysis, vaso-occlusion, and ischemia-reperfusion injury. It has been suggested, that these factors may be significant features of SCD phenotype variations.

HbS sickling can be described in terms of how fast it occurs (rate of sickling) and how much hemoglobin is being polymerized (extent of sickling). Both the rate and the extent of sickling depend on a multitude of factors including e.g. HbS concentration, pH, temperature, and level (degree) of hypoxia. Under physiological conditions the rates of oxygen binding and dissociation with hemoglobin are very fast (milliseconds), thus the ratio between oxygenated and deoxygenated Hb forms during e.g. is duration of blood flow through microcirculation is determined primarily by changes in the partial oxygen pressure in the environment. Considering the transit times, potentially affected by transient RBC adhesion to endothelium, and different and variable levels of hypoxia possible throughout the circulatory system and in the perfused organs, local levels of hypoxia would be an important factor affecting hemoglobin S polymerization.

It has been shown that for sickle RBC the type of sickled hemoglobin polymerization (resulting in potentially different hypoxic RBC morphology) depends on sickle Hb concentration, and importantly on the rate of development of hypoxemia. For example, it was shown that gradual hypoxia development and thus gradual Hb deoxygenation favors the development of so-called "sickle" and "holly leaf" RBC morphological shapes, while fast hypoxia development and thus fast Hb deoxygenation favors the development of the so-called "granular" RBC morphological state. Resultant RBC morphology is mainly determined by the total number of the aligned hemoglobin polymers and the configuration of each polymer domain in the cell. It can also depend on the cell membrane rigidity and the HbS polymer growth rate, dependent in turn on the hypoxia development rate and HbS deoxygenation. Overall, the severity of hypoxia and the rate of its development are critical parameters both in the HbS polymerization and polymer melting, with the potential to significantly affect cell membrane properties and oxygen transport.

HbS polymer melting during reoxygenation physiologically occurs in the lungs or when encountering less severe hypoxia conditions in the process of normal circulation. The process of polymer melting was shown to be dependent on multiple factors including among others, the type of polymer, $PtO_2$ of the environment and HbS reoxygenation rates.

Related to the kinetics of HbS polymerization, it has been shown that it can be described by a sigmoidal function with a delay time, which is dependent on multiple factors including e.g. HbS concentration, $PtO_2$, pH, or temperature. All of those had been shown to affect not only the extent of sickling, but the rate of sickling as well.

At physiologically-relevant RBC Hb concentrations and oxygen saturations, the delay times can range from 1 ms to >100 s, with intra cellular HbS polymerization occurring by the same nucleation and growth mechanism as in solutions of purified HbS. Separately, delay times from 0.5-2 s for capillary transit to 10-40 s for total circulation times had been reported.

The rate of sickling has been previously suggested to be an important determinant of the clinical severity. High sensitivity of polymerization (gelation) delay time to small changes in physiological parameters suggested the delay time as an extremely important variable in the disease. Increase in the delay time can significantly increase the probability of sickling within the microcirculation or venous return. A shift of the erythrocyte population from Region I toward Region IV increases the probability of sickling within the microcirculation or venous return. This shift may be brought about by several factors: the delay time is predicted to be halved by increasing the intracellular hemoglobin concentration from 34 to 35 g %, by increasing the temperature from 37 to 38.5° C., or by decreasing the intracellular pH by 0.03 unit. Although these factors have long been known to influence the thermodynamics (extent) of sickling, it also had been demonstrated that their effect on the thermodynamics is minor compared to their dramatic effect on the rate of sickling.

Despite the vast differences in hypoxic conditions and in resultant oxygenated/deoxygenated hemoglobin states throughout human body due to normal physiology, conditions, or pathologies, experiments on tissues are presently conducted either under atmospheric oxygen or at severe hypoxia conditions. Experimentation at predetermined levels of hypoxia that are found in specific tissues or as a result of specific conditions—including as the result of specific diseases such as SCD—are difficult to perform.

There are a number of conventional methods for inducing hypoxia, or oxygen scavenging, in liquids. For example, removal of dissolved gases from solutions can be performed by heating the solution with or without using vacuum pumps, or by exposing the solution to ultrasonic energy.

Both of these methods are unsuitable for use with blood and blood components, however, due to inevitable RBC damage and lysis. Equally unsuitable for use with biological system are methods which de-gas by electrically generating oxygen radicals in the water solution with dissolved oxygen in which a reducing agent has been dissolved or methods that induce formation of microbubbles to coalesce on the surface of the de-gassing. A more simple approach, would involve a direct liquid to gas exchange through the liquid surface with or without liquid agitation or gas forcibly penetration the liquid, as in "bubbling" commonly used for de-gassing small non-biological volumes. While simple, this approach is often slow and cumbersome, requiring the use of glove box or other type of an anaerobic chamber.

Modifications on this approach involve gas exchange through a gas-permeable membrane with thinner membrane allowing for more rapid oxygen diffusion to the liquid sample. The process can be accelerated with the use of thin liquid layers that decreases the time required for oxygen diffusion through the sample and can significantly reduce diffusion-generated oxygen concentration gradients through the sample thickness. Such an approach, involving a continuous-flow, steady-state apparatus that circulates a dilute RBC suspension through gas-permeable silicone tubing with segments that are exposed to either nitrogen or ambient oxygen (for sample reoxygenation) applied to the study of Red Blood Cell function under hypoxia had been described previously. Notably, for that system it was reported that the oxygenation and deoxygenation $PtO_2$ values stabilized within 30 minutes with the stabilized $PtO_2$ ranges from 25 to 37 mm Hg in the deoxygenation and from 55 to 80 mm Hg in the oxygenation when checked in Red Blood Cell (RBC) suspension. This variability in $PtO_2$ values was reported to be a contributing factor to wide range of hypoxia induced RBC target response.

Another conventional approach to inducing hypoxia in liquids introduces non-organic oxygen scavenger compounds e.g. a water-soluble transition metal compound into the solution. Such oxygen scavenging sorbents or other oxygen scrubber compounds can be isolated from the solution e.g. by a gas-permeable membrane. Such approaches had been used for example, in blood storage devices that deplete oxygen in packed RBC during storage. Alternatively, the other side of a gas-permeable membrane can be exposed to vacuum or oxygen-free gas. Flushing gas can also be used in combination with oxygen-sorbent materials. Alternatively, oxygen scavenging material can be in direct contact with the liquid (e.g. with plasma, whole blood, or RBC concentrate). That can be achieved using catalysis through precoat filters or solid catalyst.

Hypoxia can also be induced using soluble chemical oxygen scavengers like sodium dithionite (sometimes used in combination with gas-permeable enclosures), and has been used for study of red blood cell properties. However, sodium dithionite scavenging results in production of Reactive Oxygen Species (ROC), with the risk of ROC-induced damage to RBC.

Oxygen scavenging in liquids, including blood, can also be done using enzymatic catalysis. One well established example of enzyme-induced catalytic oxygen scavenging is Glucose oxidase/catalase system (GOC). Another is Pyranose Oxidase/Catalase (POC). Catalase is used to reduce the impact of a Reactive Oxygen Species (here hydrogen peroxide). Another option is the use of Protocatechuic Acid/Protocatechuate-3,4-dioxygenase system (PCA/PCD), that consumes one mole of oxygen, for each mole of PCA converted to product. Hypoxia, when induced through the PCA/PCD system, had been used previously for hemoglobin deoxygenation. Under standardized conditions, with the saturating concentration of the substrate, lower final dissolved oxygen concentrations have been observed with the PCA/PCD system than with GOC. Further, the PCA/PCD system does not generate any ROS during the catalyzed reaction with oxygen and does not interfere with independently produced ROS e.g. due to the presence of catalase as e.g. in GOC and POC oxygen scavenging systems.

Although a variety of methods are known for inducing hypoxia in liquids as described above, many of these methods cannot be used effectively or reliably when inducing hypoxia in blood for the reasons noted above. Further, even those methods that can be used effectively or reliably to induce hypoxia in blood have heretofore been used only to induce severe hypoxia in blood. As a result the methods have not been suitable for use in assessing tissues and changes in tissues under the differences in hypoxic conditions occurring throughout the human body due to normal physiology, conditions, or pathologies. Significantly, these methods have not been suitable for assessing tissues and changes in tissues occurring at different rates of increasing hypoxia (or tissue deoxygenation) and decreasing hypoxia (on tissue reoxygenation) levels, as well as at different resultant levels of deoxygenation and reoxygenation, especially, combined with multiple cycles of such hypoxia and reoxygenation. The inventors herein have recognized a need for a method and system to allow for reliable experimentation under variable hypoxic conditions and, more specifically, a need for a method and system to allow experimentation on blood samples under variable levels of hypoxemia and the rates of change in hypoxemia levels combined with the ability to repeat the process multiple times in that aspect mimicking physiological deoxygenation-reoxygenation cycling.

BRIEF SUMMARY OF THE INVENTION

This disclosure relates to methods for assessing the effects of hypoxia on tissue. In particular, this disclosure relates to a method employing a reaction substrate such as protocatechuic acid (PCA) and a reaction enzyme such as protocatechuate dioxygenase (PCD) to create hypoxia in tissue to allow for assessment of hypoxia in the tissue.

A method for assessing an effect of hypoxia on a tissue in accordance with one embodiment includes providing a sample of the tissue in a hermetically sealed container. The method further includes determining a first amount of a reaction substrate to be introduced into the sealed container and determining a second amount of a reaction enzyme to be introduced into the sealed container. The method further includes introducing the reaction substrate and the reaction enzyme into the sealed container. At least one of the first amount of the reaction substrate and the second amount of the reaction enzyme is selected to induce at least one of a predetermined amount of hypoxia less than anoxia and a predetermined rate of hypoxia in the tissue during a reaction between the reaction substrate and the reaction enzyme. In one embodiment, the reaction substrate comprises protocatechuic acid (PCA) and the reaction enzyme comprises protocatechuate dioxygenase (PCD).

In one embodiment, the method may further includes the steps of dividing the tissue in multiple samples and placing the samples in separate containers, measuring, without introducing the reaction substrate and the reaction enzyme into the sealed container containing one of the samples, a first value of a property of the tissue and measuring, after introducing the reaction substrate and the reaction enzyme into a sealed container containing another of the samples, a second value of the property of the tissue. The method may further include the step of determining the change in the value of the property responsive to the first and second values of the property.

A method for assessing an effect of hypoxia on a tissue in accordance the present teachings represents an improvement as compared to conventional methods. The disclosed method allows assessment of tissues having specific levels of hypoxia and/or rates of hypoxia. As a result, the method can be used to prepare tissue for assessment and experimentation such that the tissue reflects the many different hypoxic conditions the tissue may encounter from normal physiology, conditions, or pathologies such as SCD. The ability to differentiate damage due to application of variable levels of hypoxia can further allow taking a sample to different levels of hypoxia in multiple cycles—with such hypoxia being equivalent between cycles or varying between cycles based e.g. on changes in physiological hypoxia due to exercise or other activity, or the action of a drug or therapy. Repeat cycles of hypoxia with each cycle potentially contributing to progressive cell membrane damage adds another dimension to the assessment of the potential impact of hypoxia, including the impact on specific organs or at particular conditions (including pathological). For example, in certain cases, cell membrane damage as a result of multiple cycles of low hypoxia (e.g. 25% or 50%) may be more appropriate for physiological assessment that damage resulting from one or more cycles of severe hypoxia.

The foregoing and other aspects, features, details, utilities, and advantages of the present teachings will be apparent from reading the following description and claims, and from reviewing the accompanying drawings.

DETAILED DESCRIPTION OF THE INVENTION

Figure 1:
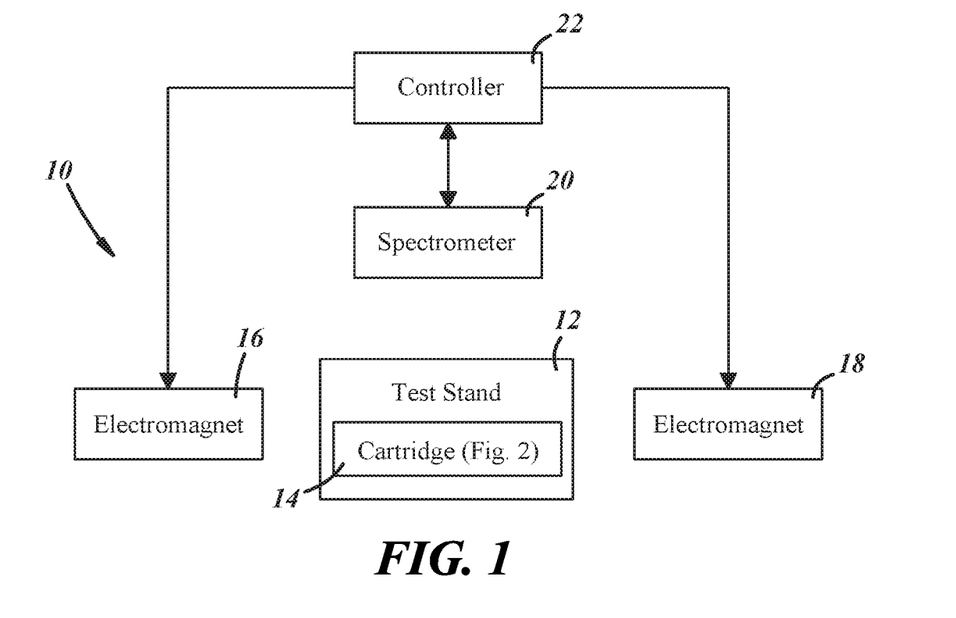
FIG. 1 is a schematic drawing of a system in accordance with one embodiment of the invention.

Referring now to the drawings wherein like reference numerals are used to identify identical components in the various views, FIG. 1 illustrates one embodiment of a system 10 for assessing an effect of hypoxia on a tissue in accordance with the present teachings. Although the system and method are described herein for use on tissue and, in particular, blood, it should be understood that the method and system as described herein could be used to induce hypoxia in any liquid or sample that is predominantly liquid.

Referring to FIG. 1, system 10 may include means, such as a test stand 12, for supporting a cartridge 14 that is used to hold a sample and is described in greater detail hereinbelow. It should be understood that the configuration of test stand 12 will depend upon the configuration of cartridge 14 as well as the surrounding equipment used to agitate the sample and take measurements of the sample.

System 10 may further include a pair of electromagnets 16, 18. Electromagnets 16, 18 are provided to agitate the sample. In particular, electromagnets 16, 18 are provided to cause movement of a magnetic bead within the sample. In the case of blood, movement of the bead causes lysis of red blood cells for evaluation of the mechanical fragility of cell membranes. Although electromagnets 16, 18 are used to agitate the sample in the illustrated embodiment, it should be understood that the sample may be agitated in other ways including by, for example, a motor that controls movement of the cartridge 14 relative to the test stand 12 or movement of the test stand 12 itself. Although the illustrated embodiment employs a pair of electromagnets, it should be understood that an alternative design could use a single electromagnet to cause movement of the magnetic bead within the sample.

System 10 may further include a spectrometer 20. Spectrometer 20 is provided to analyze the sample in the cartridge 14 by recording and measuring spectral components of electromagnetic radiation such as light passing through the sample. A radiation source, such as one or more light emitting didoes (not shown) may generate radiation that passes through the sample. Spectrometer 20 may measure absorbance of the radiation in the 530-580 nm range (typically using either 576-578 nm or 542 nm wavelength corresponding to absorbance maxima of Oxy-Hb spectrum), in the 400-450 nm range (for example using 418 nm corresponding the Soret band of the oxygenated hemoglobin spectrum) and, using absorbance at 685-700 nm as a reference after it passes through the sample in the cartridge 14.

System 10 may finally include a controller 22. Controller 22 controls the operation of electromagnets 16, 18 and spectrometer 20 and may process information generated by spectrometer 20. Controller 22 may comprise a programmable microprocessor or microcontroller or may comprise an application specific integrated circuit (ASIC). Controller 22 may include a central processing unit (CPU). Controller 22 may also include a memory and an input/output (I/O) interface through which controller 22 may receive a plurality of input signals including those generated by spectrometer 20 and transmit a plurality of output signals including those used to control electromagnets 16, 18 and spectrometer 20.

Figure 2:
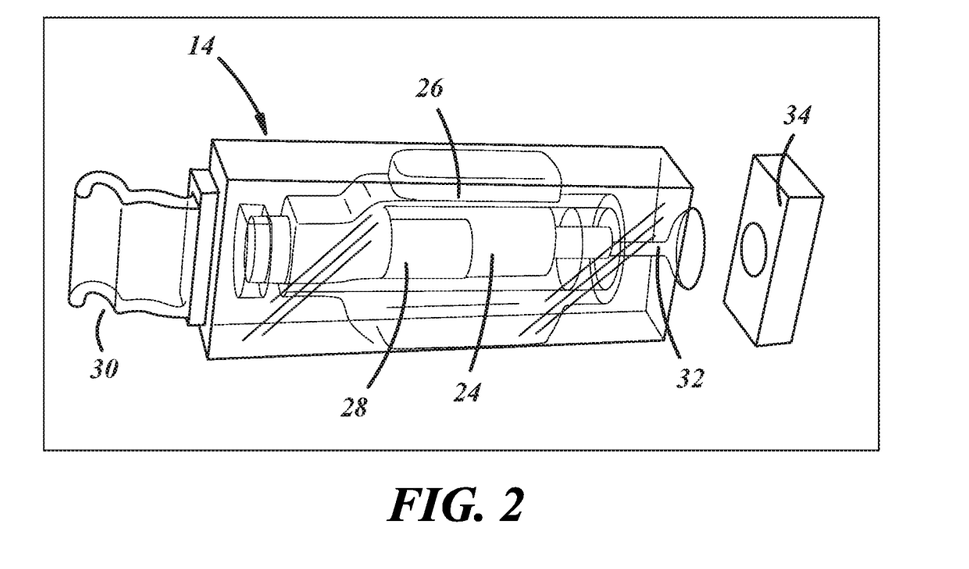
FIG. 2 is a drawing of a disposable cartridge for use in the system of FIG. 1.

Referring now to FIG. 2, one embodiment of a cartridge 14 for use in system 10 will be described in greater detail. Cartridge 14 is configured to receive a sample 24. In the illustrated embodiment, sample 24 comprise a tissue and, in particular blood. It should again be understood, however, that the sample 24 may comprise other liquids. For example, the sample 24 may comprise a red blood cell concentrate of the type used in blood transfusion. The sample may be stored in a hermetically sealed container 26 and cartridge 14 may be configured to receive and support container 26. The container 26 may include a bead 28. In the illustrated embodiment, bead 28 comprise a magnetic bead that may be moved within the container 26 under the influence of electromagnets 16, 18. Oscillation of bead 28 induce flows through the annular gap between the bead 28 and container wall with the speed of the flow regulated through the size of the gap and bead oscillation parameters (intensity, frequency). Flow velocity and type (turbulent, laminar) is the defining parameter for flow induced cell stress, and a stress with a predefined shear rate can be achieved using methods well known in the art. That allows, when necessary, to induce shear stress of desired intensity and duration while the sample 24 is at the desired level of hypoxia. Cartridge 14 may further include a capillary 32 at an opposite end configured to permit insertion of a syringe or other delivery device for injecting material into the container 26 as disused in greater detail below. A lid 34 having a capillary insert may close the end of cartridge 14 opposite hook 30, and upon being attached to the container (through, e.g., screw threads) displace any solution in capillary 32 into container 26 while ensuring hermetic sealing of the sample 24. In practice, even if small amounts of oxygen are introduced, e.g. in a form of a small bubble, that does not significantly affect the calculated deoxygenation levels and rates as discussed below. Nevertheless, the cartridge 14 is designed to minimize/eliminate the introduction of air into the container 26.

Figure 3A:
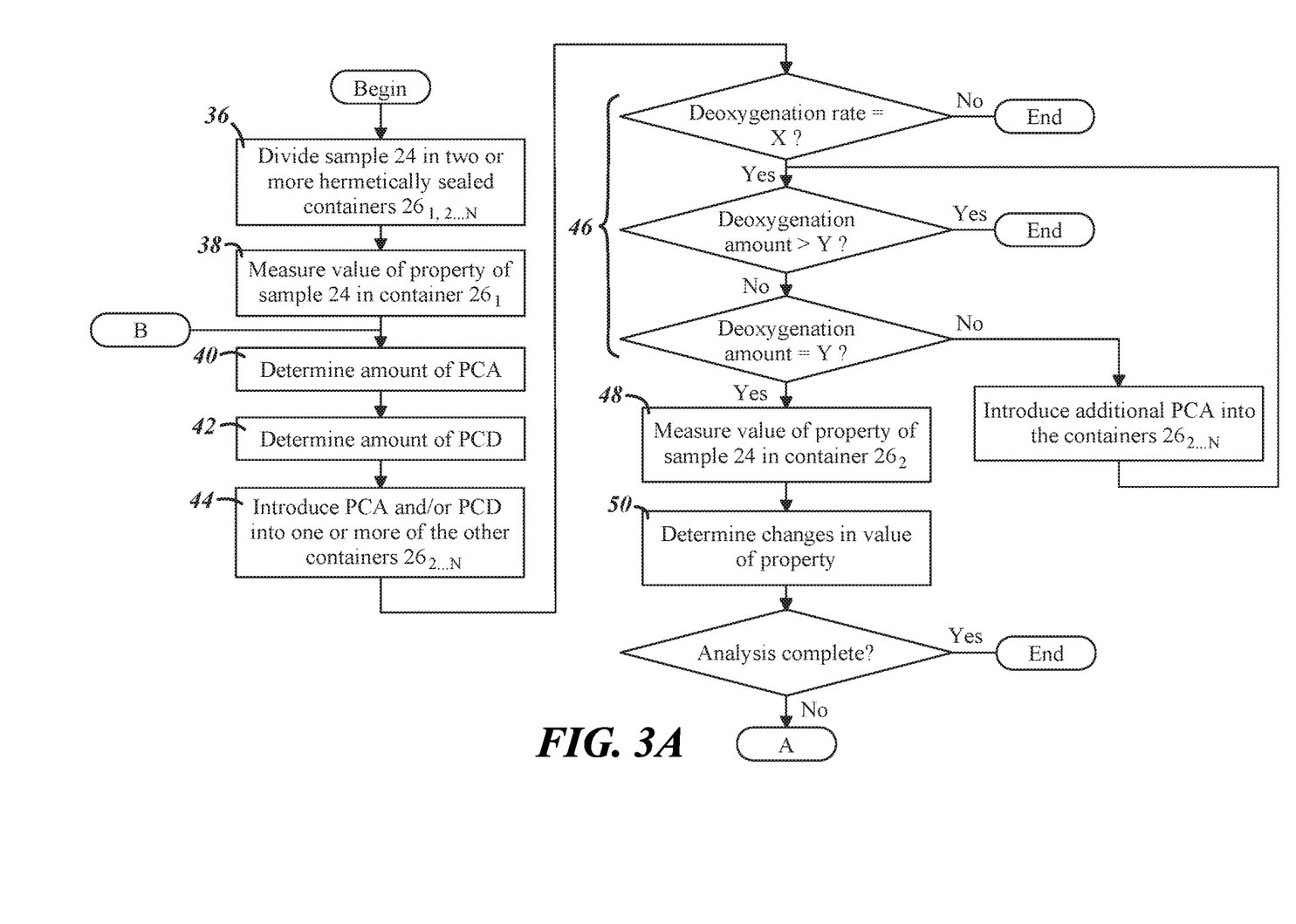
FIGS. 3A-3B are flowcharts illustrating a method in accordance with one embodiment of the invention.
Figure 3B:
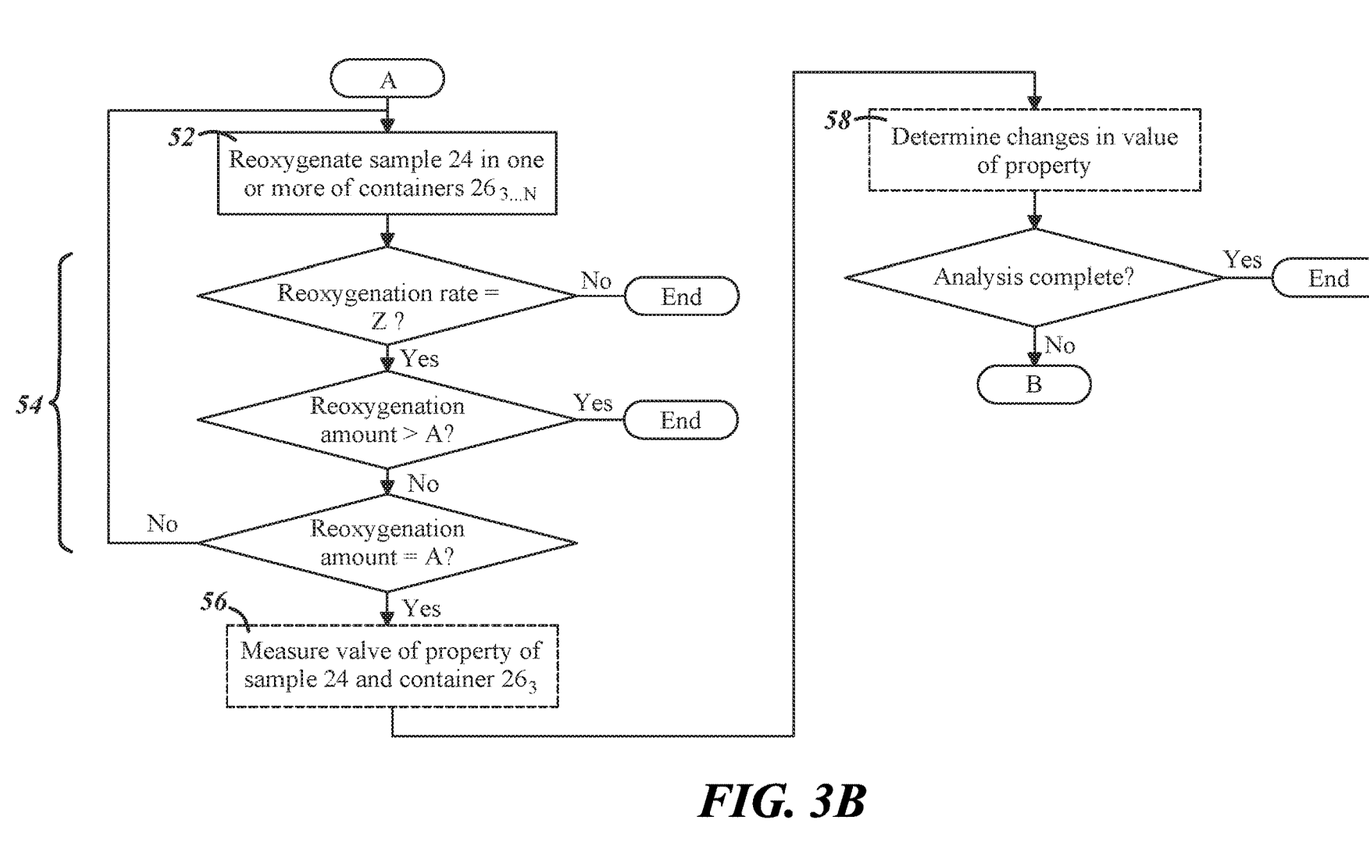

Referring now to FIGS. 3A-3B, one embodiment of a method for assessing an effect of hypoxia on a tissue in accordance with the present teachings will be described. The method may begin with the step 36 of providing one or more samples 24 of the tissue in hermetically sealed containers 26. The tissue is preferably divided into a plurality of samples 24 or aliquots with each sample 24 contained in a separate container $26_1 \ldots N$ so that measurements of a property of the tissue can be taken under a plurality of different conditions as discussed below. As discussed hereinabove, in one embodiment, the tissue may comprise blood.

The method may continue with the step 38 of measuring a first value of a property of the tissue in the sample 24 contained in one of the containers $26_1 \ldots N$. The step occurs with an unaltered sample 24—and in particular without introduction of reaction materials as described below—and therefore provides a baseline value of the property for comparison and analysis. In the case where the tissue comprises blood, the measured property may comprise the mechanical fragility (MF) of a membrane of red blood cells. In a particular application related to SCD, the property may comprise the mechanical fragility of HbS containing cells (which could be affected by HbS polymerization and oxidative damage). The mechanical fragility of red blood cells has previously been used to evaluate the potential of irreversible or poorly reversible membrane modification and the extent of plastic deformation of HbS containing cells resulting from hypoxia can potentially serve as a prognostic biomarker of disease severity and complication risk including vaso occlusive crisis (VOC). Applicant has developed proprietary assays that enable rapid and simple MF measurement by subjecting a RBC sample to varying levels of shear stress and determining the sample's susceptibility to hemolysis in real-time without requiring centrifugation. Additionally, existing technology allows for RBC MF measurements under variable levels of hypoxia (depletion of oxygen resulting in deoxyhemoglobin fraction relative to total hemoglobin concentration in the sample from 0-100%) and after consequent re-oxygenation. Such cycles can be repeated as necessary. Varying applied stress intensity and duration allows the construction of multi-dimensional fragility profiles from which various indices can be obtained (e.g. as an area under the curve of best fit to experimental data) representing in addition to total sample induced hemolysis under given stress, also RBC sub-populations varying in their response to that stress (e.g. high and low relative susceptibility to lysis). The measurement of mechanical fragility may be obtained, for example, by agitating the sample through, for example, alternate application of electromagnets 16, 18 (or application of alternating current to a single electromagnet to generate magnetic fields of changing polarity) to move (oscillate) bead 28 within the container 26 followed by directing electromagnetic radiation (e.g., light) through the sample and conducting a spectral analysis of the sample. It should be understood that a variety of properties associate with blood could be measured. It should be further understood that the properties to be measured will vary with the type of tissue or, more broadly, the type of liquid being assessed in the method.

The method may continue with the steps 40, 42 of determining an amount of a reaction substrate such as protocatechuic acid (PCA) to be introduced into another of the sealed containers $26_1 \ldots N$ containing a different sample 24 or aliquot of the tissue and determining an amount of a reaction enzyme such as protocatechuate dioxygenase (PCD) to be introduced into same sealed container 26. PCA and PCD are inputs to a catalytic reaction that will take place in container 26 to deoxygenate the sample 24 and induce hypoxia in the sample 24. In accordance with the present teachings, the amount of one or both of PCA and PCD is specifically calculated to achieve a predetermined effect in the sample 24 during the reaction between the PCA and PCD. In particular, the amount of PCA may be selected to induce a predetermined amount of hypoxia, less than anoxia, in the sample 24. The predetermined amount may correspond to a particular physiological effect (e.g., a level hypoxia resulting from physical exertion or being due to a particular elevation). The predetermined amount may alternatively correspond to a level found in a particular organ with a living body. The predetermined amount may alternatively correspond to a level corresponding a pathological condition. In accordance with one embodiment, the amount corresponds to a level associated with sickle cell disease (SCD).

The amount of PCA may be calculated based on the calculated amount of oxygen in the sample 24. Oxygen is carried in the blood both dissolved in plasma (about 0.3 vol % at $pO_2$ of 100 mm Hg typical value for arterial blood), and in water contained within RBC (about 70% of RBC volume is water), cumulatively about 2% of the total oxygen in blood, as well as reversibly bound to hemoglobin contained within the RBC (about 98% of the total). Oxygen solubility in water is rather low, with dissolved oxygen, under standard conditions, often taken at about 270 µM. More precise calculations for the plasma $O_2$ solubility can be made taking into account partial oxygen pressure in the atmosphere and temperature. Notably, dissolved oxygen concentration is known to decrease in a nonlinear manner with increasing temperature. Deviations from standard conditions (pressure, temperature, etc.) can be taken into account for more precise estimates, even though that would likely have minor impact on the results, as those are typically small compared to the amount of oxygen bound to hemoglobin (regardless of whether Hb is contained within RBC or it is free in solution). The amount of Hb-bound oxygen would be proportionate to the relative amount of oxygenated hemoglobin (hemoglobin oxygen saturation). That can be measured directly by established spectrophotometric methods or estimated based on partial oxygen pressure in the gas environment of the sample. Note, that this would be a value averaged across the sample being subject to oxygen diffusion through the medium. Also, due e.g. to stochastic variations, it would be an average of the oxygenation across all Hb monomers, and thus representing a distribution of oxygenation of Hb tetramers, similar to that occurring physiologically. That value may differ in certain pathologies, e.g. in the presence of Hb variants with altered oxygen binding capacity, which, if necessary, can be also taken into account. The total amount of oxygen would, naturally, depend on total hemoglobin concentration in the sample, which can also be determined e.g. spectrophotometrically, with a physiological range of about 12-16 g/dL for healthy donors with males having slightly more hemoglobin (~2 g/dL difference), than females. In addition to total sample hemoglobin concentration, spectrophotometric analysis can also provide direct measurement of relative oxygenated and deoxygenated hemoglobin concentrations through a multiwavelength analysis known in the art. That also can be used to improve the accuracy of the calculation of the hemoglobin-bound amount of oxygen. For example, assuming Hb concentration of 15 g/dL with and 98% saturation—reasonable for arterial blood—blood would contain a total of about 206 ml $O_2$/liter blood, with ~203 ml $O_2$/liter blood bound to hemoglobin and 3 ml $O_2$/liter blood contributed by the dissolved oxygen. PCA/PCD catalysis occurs with 1:1 oxygen consumption ration between PCA and $O_2$. Thus, for each M of PCA undergoing catalysis, 1 µM of oxygen would be consumed. That allows for easy calculation of PCA amount required to achieve desired severity of hypoxia (e.g. in terms of desired change in oxygen in media or in terms of resultant Deoxy-Hb concentration). In accordance with one embodiment, after the oxygen content in the sample 24 is determined, a high concentration stock PCA solution is prepared for addition to the sample 24. The solution may be prepared by first, if necessary, measuring the PCA concentration in the solution. The PCA concentration necessary to consume the desired amount of oxygen in the sample 24 is then calculated and, in response, the volume of the solution required to be added to the sample 24. If necessary, the solution can be deoxygenated (e.g., through gas exchange) before the calculated volume is added to the sample 24 (while prohibiting the introduction of any additional oxygen to the sample 24). While reasonably accurate PCA concentrations in solution can be achieved using analytical balance (weight of PCA by weight buffer), higher precision can be achieved by measuring PCA concentration of freshly prepared stock e.g. spectrophotometrically of by HPLC. To achieve severe (Deoxy-Hb concertation >95%) hypoxia, a saturate relative to sample oxygen, PCA concentration can be used. Note, that if stock PCA concentration is set sufficiently high, small addition of oxygen-containing PCA solution to achieve desired sample PCA concentration would result in negligible changes in sample oxygen content and can be ignored. However, if the PCA volume to be added is significant relative to the sample volume, the amount of oxygen in PCA stock to be added needs to be estimated, or alternatively, stock PCA can be deoxygenated separately e.g. through gas exchange.

Figure 4:
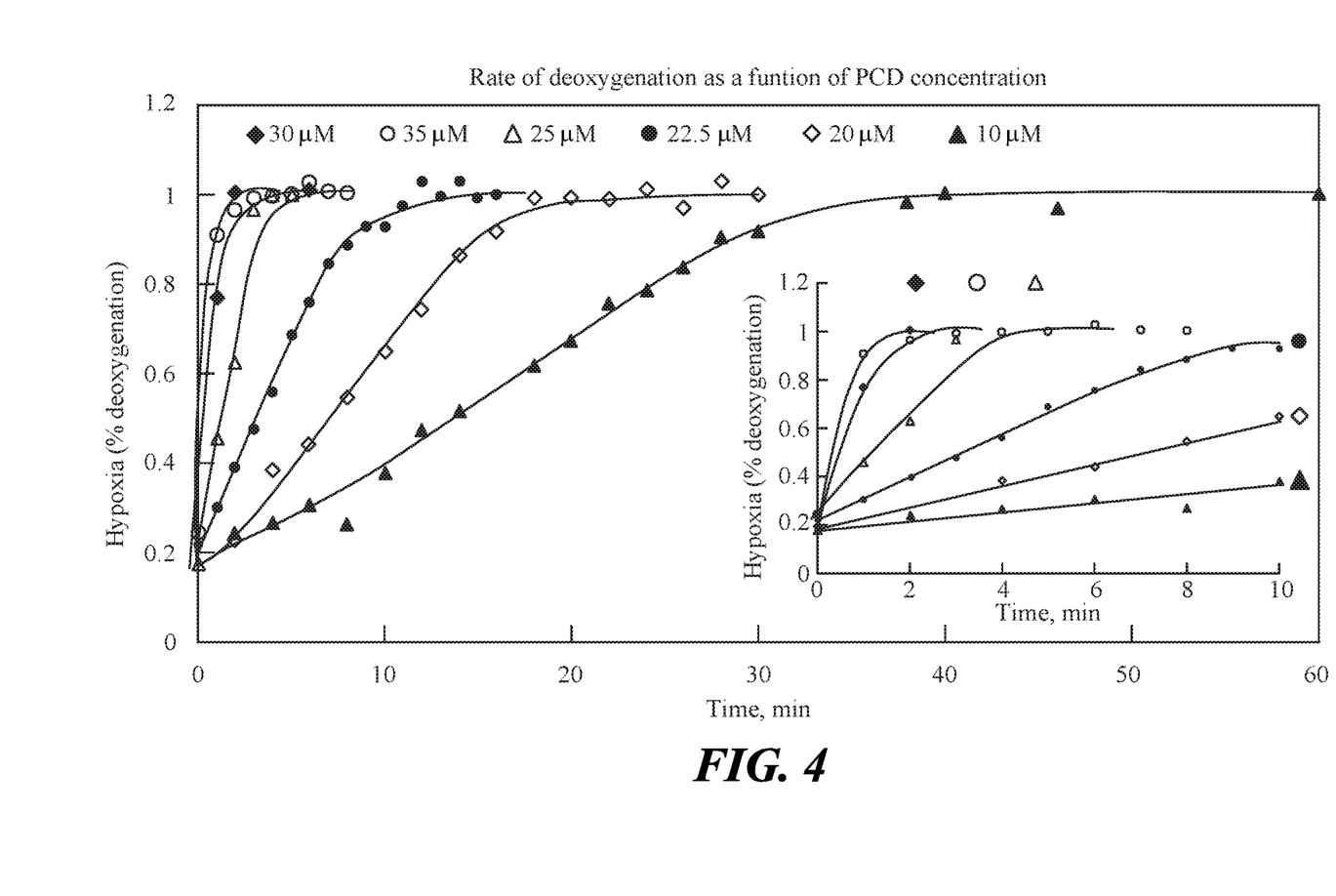
FIG. 4 is a graph illustrating a rate of deoxygenation in whole blood as a function of the amount of PCD.

The amount of PCD may alternately, or in addition, be selected to induce a predetermined rate of hypoxia in the sample 24. The predetermined rate may again correspond to a particular physiological effect or rate corresponding to a particular organ with a living body or pathological condition. In accordance with one embodiment, the rate corresponds to a level associated with sickle cell disease (SCD) and, in particular, may correspond to a rate of development of a predetermined sickled red blood cell morphological form. A predetermined rate of hypoxia as used herein should be understood as a predefined rate of change in partial oxygen pressure in a sample due to a predefined rate of oxygen consumption. The predetermined rate, and the required amount of PCD, can be calculated e.g. using enzyme turnover number (TN, $s^{-1}$) and its concentration (C, µM). The rate of oxygen consumption (R) with thus be given by the equation: $R=TN*C$ (µM/s). Enzyme concentration and TN can be measured separately, or alternatively, PCD oxygen consumption rate can be determined for a particular enzyme sample through consumption of a known amount of oxygen e.g. using oxygen electrode and expressed in units of enzyme's catalytic activity (U or UI), that directly represent the amount of the enzyme that catalyzes the conversion of one micromole of substrate per minute under a given assay conditions as shown in FIG. 4. As conversion of 1 µM of PCA means consumption of 1 µM $O_2$, rates of oxygen consumption and thus the desired rate of hypoxic condition development can be calculated Where the sample 24 has been divided into more than two aliquots, steps 40, 42 may be performed multiple times to establish different amounts of PCA and PCD corresponding to different predetermined amounts of hypoxia. less than anoxia, in the sample 24 and/or different predetermined rates of hypoxia in the sample 24.

The method may further include the step 44 of introducing the reaction substrate and the reaction enzyme into the sealed container 26. Referring to FIG. 2, PCA and PCD can be introduced into container 26 by injecting PCA and/or PCD into the sample through the capillary 32 using a Hamilton syringe or similar structure, displacing the proportionate volume of sample 24 from the capillary 32 end, and then screwing lid 34 onto container 26 to hermetically seal it. Opening the lid would not violate the anaerobicity of the sample 24 due to extremely slow oxygen diffusion rates through the capillary 32. Alternatively, addition of PCA or PCD to sample 24 could be done through a wall of container 26 with the material of container 26 selected to seal any small puncture after an introducing needle is withdrawn. In this case, the volume of the material added to the sample should be sufficiently small to avoid any measurable increase in the internal pressure. An increase in pressure could be a confounding factor for RBC MF measurement of hypoxic sample, but obviously not of re-oxygenated one. Again, where the sample 24 has been divided into more than two aliquots, step 44 may be performed multiple times to induce different amounts or rates of hypoxia in the portions of sample 24 in each container 26.

The method may continue with the step 46 of verifying that the amount of hypoxia in the sample 24 and/or the rate of hypoxia in the sample 24 following the catalytic reaction between the PCA and PCD introduced to the container 26 in step 44 meets a predetermined condition relative to the predetermined amount of hypoxia or predetermined rate of hypoxia, respectively, in the sample 24. The predetermined condition may, for example require that the amount and/or rate of hypoxia equal the predetermined amount or rate or fall within an acceptable range relative to the predetermined amount/rate. In the illustrated embodiment, step 46 may begin by verifying that the rate of hypoxia in the sample equals a predetermined rate. If it does not, the sample 24 cannot be used for testing and the process may be terminated. If the rate of hypoxia equals the predetermined rate, the system may proceed to determine whether the amount of hypoxia exceeds a predetermined amount. If it does, the sample 24 again is not suitable for testing and the process may be terminated. If the amount of hypoxia does not exceed the predetermined amount, the system determines whether the amount of hypoxia equals the predetermined amount. If it does not, additional PCA may be introduced into the container 26 until the amount of hypoxia equals the predetermined amount. Step 46 may be performed by measuring a concentration of deoxygenated hemoglobin in the sample and/or a deoxygenation rate of hemoglobin. The concentration of deoxygenated hemoglobin can be measured spectrophotometrically using the difference in absorption between oxygenated and deoxygenated hemoglobin forms in, e.g., the 500-700 nm wavelength range. The rate of deoxygenation can be determined by taking measurements over time (plotting percent of deoxygenated hemoglobin over time). In samples of whole blood or blood concentrates, hemoglobin is contained within erythrocytes, with no or minimal amount of hemoglobin free in the solution. In other cases, e.g. when hemolyzed products or just hemoglobin solutions are used, a more significant portion, or all hemoglobin may be free in solution, and not within the cells. In all cases heme contained within hemoglobin monomers binds oxygen on a 1:1 heme to oxygen basis. Hemoglobin concentration is often given for a tetramer, as each functional hemoglobin molecule contains four αβ monomer subunits, each containing one heme group. Thus, in terms of a tetramer, hemoglobin would bind four oxygen molecules per hemoglobin molecule. Here we would refer to "hemoglobin concentration" in terms of a tetramer.

If an appropriate amount and/or rate of hypoxia are determined in step 46, the method may continue with the step 48 of measuring a second value of the property, first measured in step 38, of the tissue in sample 24. Step 48 is performed on an aliquot of the sample into which the PCA and PCD have been introduced in step 44. Measurement of the second value of the property is preferably performed in the same manner as in step 38. Again, where the sample 24 has been divided into more than two aliquots, step 48 may be performed on each aliquot of the sample into which PCA and PCD have been introduced in step 44 in order to generate a second value of the property, a third value of the property, etc.

The method may then continue with the step 50 of determining one or more changes in the value of the property responsive to the values of the property measured in steps 38 and 48. Controller 22 may, for example, process the values as received from spectrometer 20 and generate one or more outputs indicative of changes in the value of the property (e.g., to a conventional output device such as a display screen). Controller 22 may determine a change in the value of the property responsive to the value obtained in step 38 (prior to introduction of any PCA/PCD to the sample) and one of the values obtained in step 48. Controller 22 may also determine a change in the value of the property responsive to two values obtained in step 48 (i.e., from aliquots into which different amounts of PCA and/or PCD were introduced).

Figure 5A:
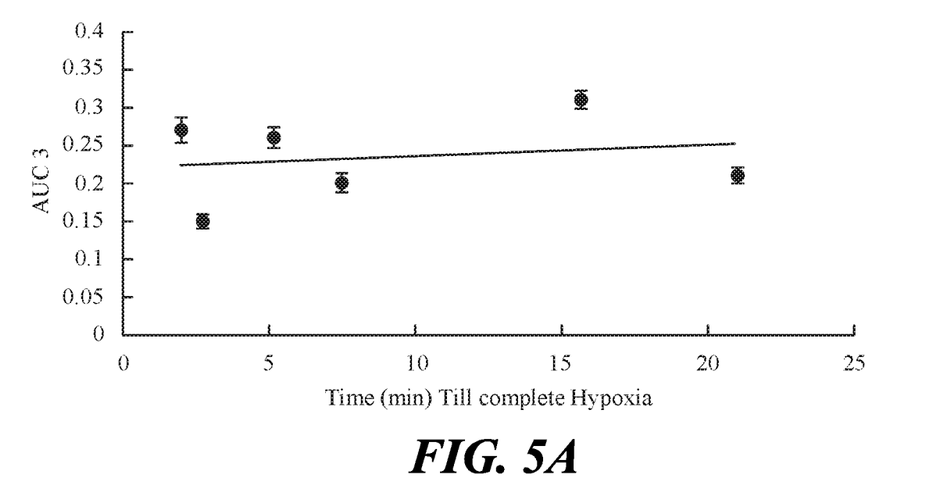
FIGS. 5A-5B are graphs illustrating the mechanical fragility of red blood cells in a donor without sickle cell disease (HbA) as a function of deoxygenation rate for small (AUC3) and large (AUC10) stress magnitudes.
Figure 5B:
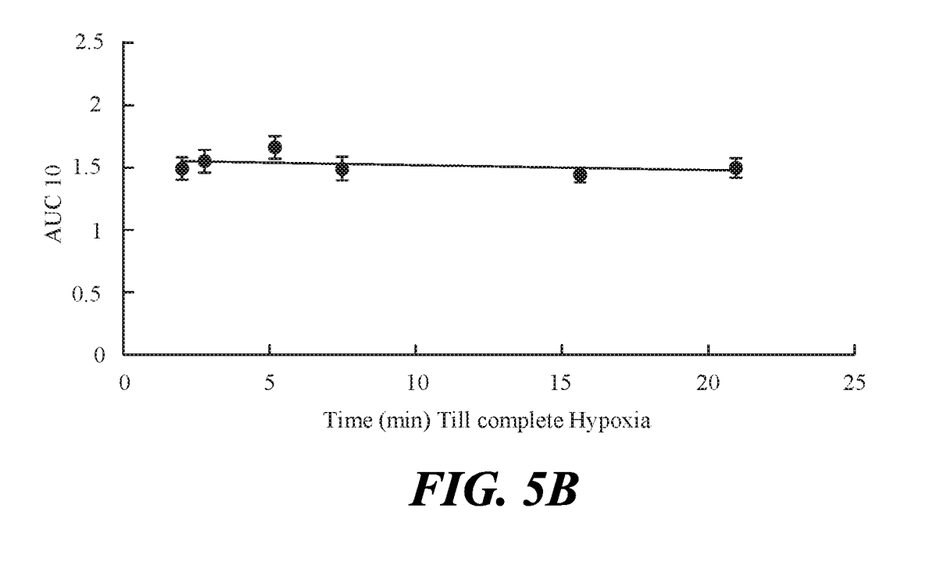
Figure 6A:
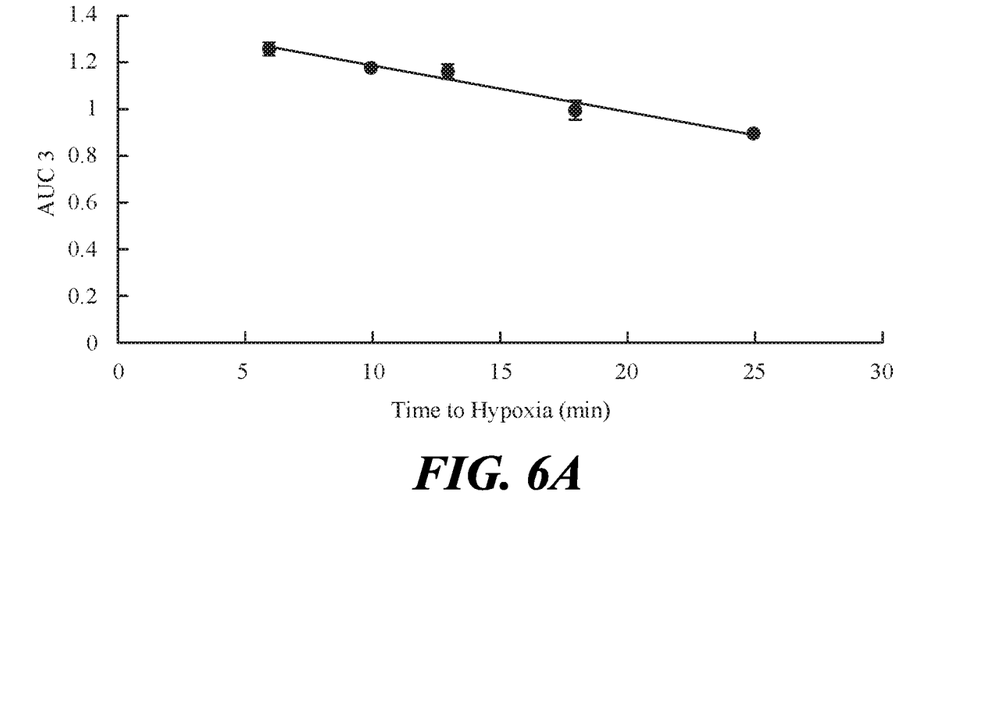
FIGS. 6A-6B are graphs illustrating the mechanical fragility of red blood cells in a donor with sickle cell disease (HbS) as a function of deoxygenation rate for small (AUC3) and large (AUC10) stress magnitudes.
Figure 6B:
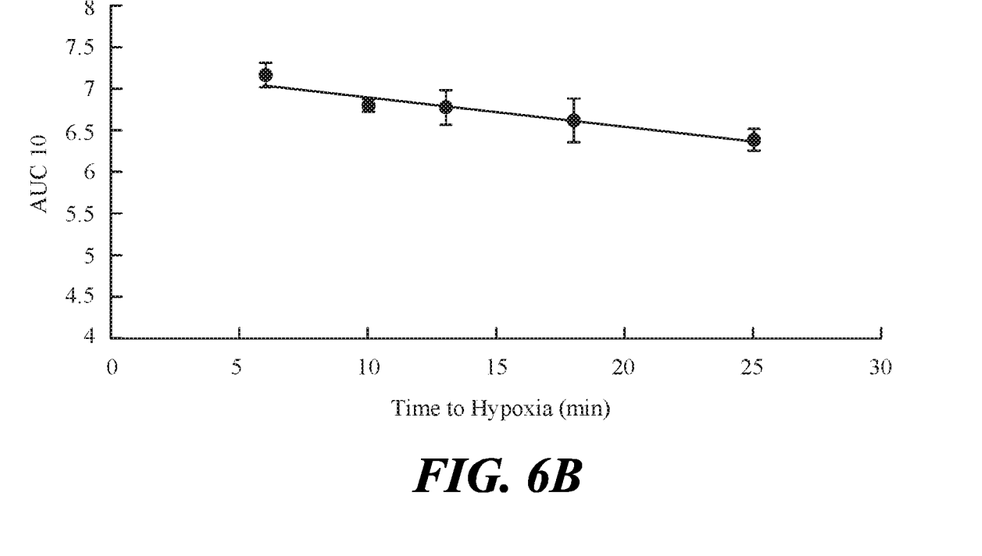

Once the PCA/PCD reaction in a given aliquot is complete and any measurements taken, the method may continue, if desired, with the step 52 of introducing oxygen into one of the sealed containers $26_1 \ldots N$ that was deoxygenated in step 44 to reoxygenate the portion of the sample 24 in the container to normoxia or a level less than normoxia. This action must be performed on a sample or aliquot in which the measurement step 48 has not been performed. Oxygen may again be introduced through capillary 32 or the sample may be taken out of the container 26 to be oxygenated (e.g., in a separate open to air vessel. In accordance with one aspect of the present teachings, the amount of PCA and/or the amount of PCD may alternatively, or in addition, be selected to induce a predetermined rate of reoxygenation of the tissue upon introduction of the oxygen. Referring to FIGS. 5A-B and 6A-B, a comparison is shown illustrating the difference impact of a predetermined rate of hypoxia (for severe hypoxia) on red blood cells from a normal donor (HbA; FIGS. 5A-B) and sickle cell patient (HbS, FIGS. 6A-B) with RBC mechanical fragility expressed as an Area Under the Curve (AUC) for two different stress magnitudes: (i) small (AUC3) and large (AUC10). In the examples shown in FIGS. 5A-B and 6A-B, samples were deoxygenated using a saturating concentration of PCA and variable amounts of PCD calculated to provide a range of deoxygenation rates, presented here in terms of time to full deoxygenation (>95% Deoxy-Hb). Deoxygenated samples were re-oxygenated under atmospheric oxygen. The magnitude of the change in mechanical fragility of RBC from healthy donors (HbA) due to cells' exposure to hypoxia and follow-up re-oxygenation did not depend on the deoxygenation rate (see FIGS. 5A-B). However, for RBC from sickle patients (HbS) the rate of sample deoxygenation had a significant effect on the change in mechanical fragility, indicating that more rapid deoxygenation induced larger damage to cell membrane, thus making RBC less resistant to mechanical stress (see FIGS. 6A-B). This indicates that faster deoxygenation, likely correlated with more rapid HbS polymerization and potentially different HbS polymers (e.g., in polymer sizes or in the number of polymerization points of origin) resulted in larger damage to RBC membrane demonstrating that the system and method described herein can be used to assess hypoxia/polymerization-induced damage on the RBC membrane.

In general, a hermetic sealed sample 24 can be kept at an established hypoxia severity (e.g. fully or partially deoxygenated) indefinitely. For a fully deoxygenated sample, PCA not consumed in the reaction (excess PCA) would help preserve anaerobicity by safeguarding against any possible oxygen contamination. As soon as the hermetic seal is breached oxygen would diffuse into a hypoxic sample. At that time, oxygen uptake by hemoglobin would compete with oxygen consumption in a reaction with PCA that is catalyzed by PCD. Practically, when sufficient amounts of PCA are present, the PCA/PCD system has been shown to keep the sample essentially anaerobic with hemoglobin remaining in its deoxygenated form. PCA in an amount over that required for initial sample deoxygenation (i.e. exceeding that required for consumption of dissolved oxygen initially present in the solution combined with the oxygen amount initially bound to hemoglobin) would react with diffusing oxygen keeping the solution anaerobic until all excess PCA is consumed The rate of diffusion, in turn, would be positively affected by, e.g., increase in temperature, increase in partial pressure of the solute (oxygen), decrease in liquid viscosity (e.g., solution with lower hematocrit), or increase in surface area of the solution exposed to oxygen-containing atmosphere as well as be significantly affected by liquid agitation required to promote homogenous oxygen distribution throughout the liquid medium. The rate of oxygen consumption would be enhanced by an increase in PCD concentration and its activity as described above. Thus, at a given excess PCA concentration, the duration of hypoxia in non-anaerobic (e.g. post-hypoxic) conditions could be modulated by changes in the ratio (R) of the rates of oxygen consumption caused by PCA/PCD/Oxygen reaction and oxygen diffusion into the medium. At a given oxygen diffusion rate and a given enzyme activity, it would then be a function of PCD concentration alone. Consistent and homogeneous oxygen diffusion rate could be achieved e.g. by gentle sample mixing under oxygen-containing atmosphere. The rate of diffusion can be varied e.g. by changing oxygen content in such atmosphere with higher $PtO_2$ resulting is higher oxygen diffusion rates. Oxygen consumption, as mentioned, can be varied by changes in PCD concentration, with higher PCD concentrations resulting in higher oxygen consumption rates. Similarly, for a fixed diffusion rate (same $O_2$ concentration, temperature and method of liquid exposure to gas phase), PCD concentration and turnover rate resulting in given oxygen consumption rate, the determining factor for severe hypoxia duration would be the excess PCA concentration. Such can thus be adjusted to create a desired delay between the breach of anaerobicity and return to oxygenated condition (e.g. return to normoxia). Different behavior can be expected in cases when the rate of oxygen consumption caused by PCA/PCD/Oxygen reaction in less than the rate of oxygen diffusion into medium (R<1) and when it is larger than the diffusion rate (R>1). Compare FIGS. 7-9. When R is less than 1, there is no delay in the onset of reoxygenation, and its rate would be determined by the difference between the rates of oxygen diffusion and consumption in the medium. That rate remains constant until all excess PCA is consumed after which time the rate changes to that of oxygen diffusion into the medium. When R is more than 1, there is a delay before the onset of reoxygenation would be determined by the amount of excess PCA and the rate of reoxygenation would be determined by oxygen diffusion rate alone. For HbS containing blood from sickle cell disease patients, changes in oxygen availability in the presented scenarios would modulate HbS polymer melting rates allowing, e.g. experimental modeling of physiological subject-specific and/or organ-specific polymer melting rates to allow for better prediction of RBC sickling in circulation and associated events like enhanced RBC adhesion to endothelium and VOC.

Figure 7:
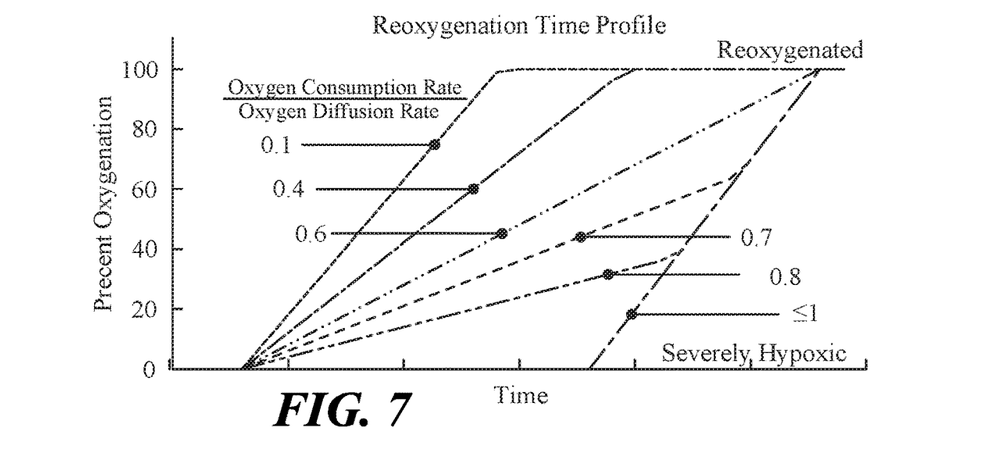
FIGS. 7-9 are graphs illustrating reoxygenation of red blood cells over time.
Figure 8:
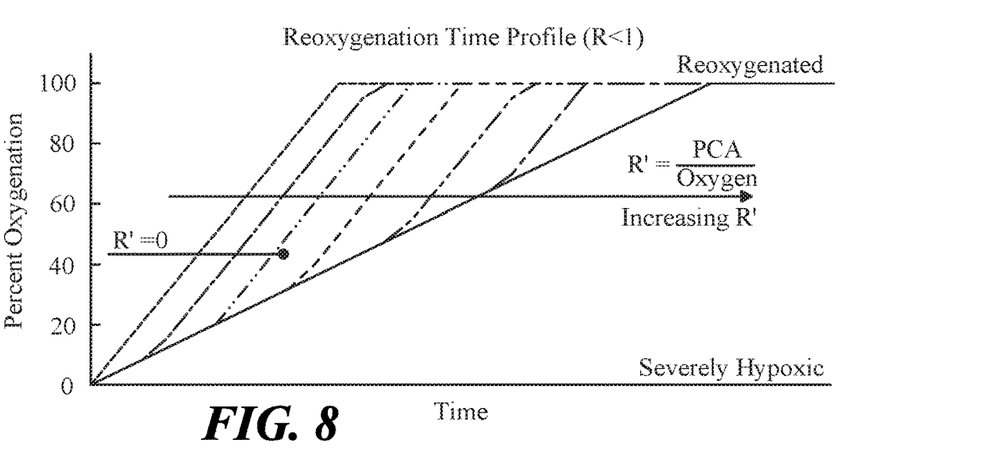
Figure 9:
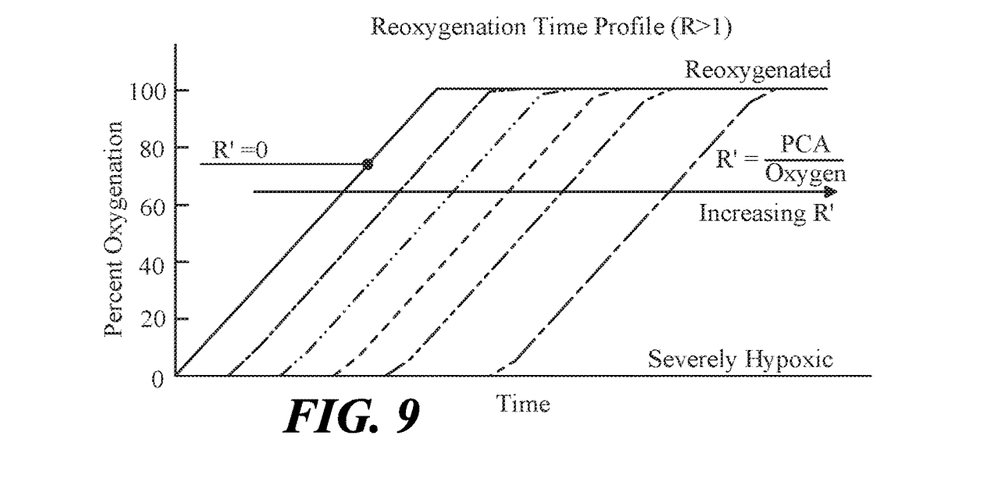

The calculations presented in FIGS. 7-9 assume fast equilibrium of hemoglobin-oxygen complex with the changing oxygen concentration in the medium (rates of changes in media $PtO_2$ are much smaller that the rates of Hb-oxygen binding or dissociation rates, as applicable). In general terms, observed rates of change ($R^{Observed}$) of oxygen concentration in the medium (plasma, buffer solution) could be modified by oxygen dissociation from hemoglobin ($R^{Dissociation}$) in case of sample deoxygenation or oxygen binding to hemoglobin ($R^{binding}$). Assuming the oxygen consumption rate due to PCA/PCD reaction ($R^{Consumption}$) and oxygen diffusion rate into the sample ($R^{Diffusion}$) $R^{Observed}=R^{Diffusion}-R^{Consumption}+R^{Dissociation}$; if $R^{Diffusion}>R^{Consumption}$ (sample re-oxygenation), or $R^{Observed}=R^{Consumption}-R^{Diffusion}+R^{Binding}$; if $R^{Diffusion}<R^{Consumption}$ (sample de-oxygenation) Note, that while $R^{Diffusion}$ and $R^{Consumption}$ can be constant, $R^{Dissociation}$ and $R^{Binding}$ would be dependent on $pO_2$ in the medium, with the changes in rate corresponding to sigmoidal hemoglobin-oxygen binding curve. Practically, $R^{Consumption}$ can be adapted (e.g. empirically, through changing PCD concentration) for a given experimental set-up with a given $R^{Diffusion}$ to achieve a desired a desired $R^{Consumption}/R^{Diffusion}$ ratio and thus desired Hb deoxygenation or re-oxygenation rate.

It should be noted, that areas of non-linearity would exist at time zero after the initiation of the reaction by addition of PCA (to sample pre-loaded with PCD) or PCD (to sample pre-loaded with PCA) and at the end of the reaction e.g. when most of the substrate or oxygen is consumed. While the impact of this non-linearity is typically small, it can be accounted for through the use of calibration curves measured in solutions with known oxygen concentration. Similarly, deviations from such could potentially be indicative of changes in oxygen availability for the reaction e.g. due to altered strength of $O_2$-Heme binding.

While the above approaches are described for an isolated system, similar results can be achieved in an open to air system as well, if oxygen diffusion into the sample is properly accounted for. In the simplest case when full sample deoxygenation is desired, an excess amount of PCA can be used to keep sample anaerobic even in the presence of atmospheric oxygen. For a given PCA amount—in excess of that required for consumption of oxygen inherently contained in the sample, including that bound to Hb-time of anaerobicity would be extended if oxygen diffusion into the sample is minimized e.g. through reducing the open to air surface area, avoidance of sample agitation, or by reducing oxygen content in the relevant gas phase e.g. by overlaying the sample with argon. Note, that ongoing oxygen diffusion into the sample would not only affect deoxygenation rates but can also allow for re-oxygenation. For example, in the case of RBC, oxygen diffusion into sample being deoxygenated, can potentially cause re-oxygenation of already deoxygenated hemoglobin, in effect subjecting a fraction or all sample to multiple oxygenation/reoxygenation cycles during deoxygenation step.

The method may further include the step 54 of verifying that the amount of reoxygenation in the sample 24 and/or the rate of reoxygenation in the sample 24 in step 52 meets a predetermined condition relative to the predetermined amount of reoxygenation or predetermined rate of reoxygenation, respectively, in the sample 24. The predetermined condition may, for example require that the amount and/or rate of reoxygenation equal the predetermined amount or rate or fall within an acceptable range relative to the predetermined amount/rate. In the illustrated embodiment, step 54 may begin by verifying that the rate of reoxygenation in the sample equals a predetermined rate. If it does not, the sample 24 cannot be used for testing and the process may be terminated. If the rate of reoxygenation equals the predetermined rate, the system may proceed to determine whether the amount of reoxygenation exceeds a predetermined amount. If it does, the sample 24 again is not suitable for testing and the process may be terminated. If the amount of reoxygenation does not exceed the predetermined amount, the system determines whether the amount of reoxygenation equals the predetermined amount. If it does not, oxygen may continue to be introduced to the container 26 until the amount of reoxygenation equals the predetermined amount. Step 54 may be performed by measuring a concentration of oxygenated hemoglobin in the sample and/or a reoxygenation rate of hemoglobin. The concentration of oxygenated hemoglobin can be done spectrophotometrically using the different in absorption between oxygenated and deoxygenated hemoglobin forms in, e.g., the 500-700 nm wavelength range. The rate of reoxygenation can be determined by taking measurements over time (plotting percent of reoxygenated hemoglobin over time).

Once the sample 24 has been reoxygenated to a desired amount, the method may continue with the optional steps 56, 58 of measuring another value of the property, previously measured in steps 38 and 48, of the tissue in sample 24 and determining one or more changes in the value of the property responsive to the values of the property measured in step 56 relative to the values measured in steps 38 and/or 48. Measurement of the value of the property is preferably performed in the same manner as in steps 38 and 48. Step 58 may again be performed by controller 22. Controller 22 may, for example, process the values as received from spectrometer 20 and generate one or more outputs indicative of changes in the value of the property (e.g., to a conventional output device such as a display screen). Controller 22 may determine a change in the value of the property as measured in step 56 relative to the value previously obtained in step 38 (prior to introduction of any PCA/PCD to the sample) and/or step 48 (after introduction of PCA/PCD to the sample).

For any samples or aliquots that undergo reoxygenation in step 52 and which do not undergo measurement in step 56, the deoxygenation process (steps 40-46) and reoxygenation process (52-54) may be repeated as many times as desired until a measurement of the particular aliquot or sample is taken (step 48 or step 56) permitting, for example, comparisons of values of the property under normoxic conditions (step 38), hypoxic conditions (initial instance of step 48) and a return to normoxic conditions (initial instance of step 56), and repeated cycles of hypoxia and returns to normoxic conditions (subsequent instances of steps 48 and 56) to provide information on cellular response to the hypoxic cycle. The pH of the sample may be monitored during this repetition to avoid changes that may affect cell properties. Buffers like HEPES can be used to avoid pH decline during the process.

While the invention has been shown and described with reference to one or more particular embodiments thereof, it will be understood by those of skill in the art that various changes and modifications can be made without departing from the spirit and scope of the invention. For example, the over molding and clamping technology disclosed herein is not limited to wheel speed sensors, but may also be used for other sensors having similar mounting arrangements including transmission sensors and crankshaft sensors.

What is claimed is:

1. A method for assessing an effect of hypoxia on a tissue, comprising the steps of:
    providing a first sample of the tissue in a first hermetically sealed container;
    determining a first amount of a reaction substrate to be introduced into the first hermetically sealed container;
    determining a second amount of a reaction enzyme to be introduced into the first hermetically sealed container;
    introducing the reaction substrate and the reaction enzyme into the first hermetically sealed container
    wherein at least one of the first amount of the reaction substrate and the second amount of the reaction enzyme is selected to induce at least one of a predetermined amount of hypoxia less than anoxia and a predetermined rate of hypoxia in the first sample of the tissue during a reaction between the reaction substrate and the reaction enzyme
    wherein the reaction substrate comprises protocatechuic acid.

2. The method of claim 1 wherein the reaction enzyme comprises protocatechuate dioxygenase.

3. The method of claim 1 wherein the tissue comprises blood.

4. The method of claim 3, further comprising the step of measuring a concentration of deoxygenated hemoglobin.

5. The method of claim 3, further comprising the step of measuring a deoxygenation rate of hemoglobin.

6. The method of claim 1 wherein the at least one of a predetermined amount of hypoxia and a predetermined rate of hypoxia corresponds to an amount of hypoxia or a rate of hypoxia associated with a disease.

7. The method of claim 6 wherein the disease comprises sickle cell disease.

8. The method of claim 7 wherein the predetermined rate of hypoxia corresponds to a predetermined sickled red blood cell morphological form.

9. The method of claim 1, further comprising the step of introducing, after the reaction is complete, oxygen to the sample, with at least one of the first amount of the reaction substrate and the second amount of the reaction enzyme selected to induce a predetermined rate of reoxygenation of the tissue upon introduction of the oxygen.

10. The method of claim 1, further comprising the steps of:
    dividing the tissue into a plurality of samples including the first sample and a second sample;
    placing the second sample of the tissue in a second hermetically sealed container;
    measuring, after introducing the reaction substrate and the reaction enzyme into the first hermetically sealed container, a first value of the property of the tissue;
    measuring, without introducing the reaction substrate and the reaction enzyme into the second hermetically sealed container, a second value of a property of the tissue; and,
    determining the change in the value of the property responsive to the first and second values of the property.

11. The method of claim 10 wherein the tissue comprises blood and the property comprises mechanical fragility of a membrane of a red blood cell.

12. The method of claim 10, further comprising the steps of:
    placing a third sample of the tissue in a third hermetically sealed container, the third sample of the tissue in the third hermetically sealed container having an initial oxygenation level;
    determining a third amount of the reaction substrate to be introduced into the third hermetically sealed container;
    determining a fourth amount of the reaction enzyme to be introduced into the third hermetically sealed container;
    introducing the third amount of the reaction substrate and the fourth amount of the reaction enzyme into the third hermetically sealed container to establish a reaction in the third hermetically sealed container;
    introducing, after the reaction is complete in the third hermetically sealed container, oxygen to the sample of the third hermetically sealed container, with at least one of the third amount of the reaction substrate and the fourth amount of the reaction enzyme selected to induce a predetermined rate of reoxygenation of the third sample of the tissue upon introduction of the oxygen; and,
    measuring, after reoxygenation of the third sample of the tissue to the initial oxygenation level, a third value of the property of the tissue; and,
    determining the change in the value of the property responsive to the second and third values of the property.

13. The method of claim 12 wherein the tissue comprises blood and the property comprises mechanical fragility of a membrane of a red blood cell.

14. The method of claim 12 wherein the oxygen comprises atmospheric oxygen.

15. A method for assessing an effect of hypoxia on a tissue, comprising the steps of:
    providing a first sample of the tissue in a first hermetically sealed container;
    determining a first amount of a reaction substrate to be introduced into the first hermetically sealed container;
    determining a second amount of a reaction enzyme to be introduced into the first hermetically sealed container;

introducing the reaction substrate and the reaction enzyme into the first hermetically sealed container wherein at least one of the first amount of the reaction substrate and the second amount of the reaction enzyme is selected to induce at least one of a predetermined amount of hypoxia less than anoxia and a predetermined rate of hypoxia in the first sample of the tissue during a reaction between the reaction substrate and the reaction enzyme wherein the reaction enzyme comprises protocatechuate dioxygenase.

16. The method of claim 15 wherein the tissue comprises blood.

17. The method of claim 16, further comprising the step of measuring a concentration of deoxygenated hemoglobin.

18. The method of claim 16, further comprising the step of measuring a deoxygenation rate of hemoglobin.

19. The method of claim 15 wherein the at least one of a predetermined amount of hypoxia and a predetermined rate of hypoxia corresponds to an amount of hypoxia or a rate of hypoxia associated with a disease.

20. The method of claim 19 wherein the disease comprises sickle cell disease.

21. The method of claim 20 wherein the predetermined rate of hypoxia corresponds to a predetermined sickled red blood cell morphological form.

22. The method of claim 15, further comprising the step of introducing, after the reaction is complete, oxygen to the sample, with at least one of the first amount of the reaction substrate and the second amount of the reaction enzyme selected to induce a predetermined rate of reoxygenation of the tissue upon introduction of the oxygen.

23. The method of claim 15, further comprising the steps of:
dividing the tissue into a plurality of samples including the first sample and a second sample;
placing the second sample of the tissue in a second hermetically sealed container;
measuring, after introducing the reaction substrate and the reaction enzyme into the first hermetically sealed container, a first value of the property of the tissue;
measuring, without introducing the reaction substrate and the reaction enzyme into the second hermetically sealed container, a second value of a property of the tissue; and,
determining the change in the value of the property responsive to the first and second values of the property.

24. The method of claim 23 wherein the tissue comprises blood and the property comprises mechanical fragility of a membrane of a red blood cell.

25. The method of claim 23, further comprising the steps of:
placing a third sample of the tissue in a third hermetically sealed container, the third sample of the tissue in the third hermetically sealed container having an initial oxygenation level;
determining a third amount of the reaction substrate to be introduced into the third hermetically sealed container;
determining a fourth amount of the reaction enzyme to be introduced into the third hermetically sealed container;
introducing the third amount of the reaction substrate and the fourth amount of the reaction enzyme into the third hermetically sealed container to establish a reaction in the third hermetically sealed container;
introducing, after the reaction is complete in the third hermetically sealed container, oxygen to the sample of the third hermetically sealed container, with at least one of the third amount of the reaction substrate and the fourth amount of the reaction enzyme selected to induce a predetermined rate of reoxygenation of the third sample of the tissue upon introduction of the oxygen; and,
measuring, after reoxygenation of the third sample of the tissue to the initial oxygenation level, a third value of the property of the tissue; and,
determining the change in the value of the property responsive to the second and third values of the property.

26. The method of claim 25 wherein the tissue comprises blood and the property comprises mechanical fragility of a membrane of a red blood cell.

27. The method of claim 25 wherein the oxygen comprises atmospheric oxygen.

* * * * *